(12) United States Patent
Yamamoto et al.

(10) Patent No.: US 6,930,083 B2
(45) Date of Patent: Aug. 16, 2005

(54) ISOMER COMPOSITION EXCELLENT IN CHEMICAL RESISTANCE CONTAINING OPTICALLY ACTIVE TRANS-1-(2,2,6-TRIMETHYLCYCLOHEXYL)-2-BUTEN-1-ONE AND FRAGRANCE COMPOSITIONS CONTAINING THE ISOMER COMPOSITION

(75) Inventors: Takeshi Yamamoto, Hiratsuka (JP); Shinya Watanabe, Hiratsuka (JP); Hideo Ujihara, Hiratsuka (JP); Toshimitsu Hagiwara, Hiratsuka (JP)

(73) Assignee: Takasago International Corporation, Tokyo (JP)

( * ) Notice: Subject to any disclaimer, the term of this patent is extended or adjusted under 35 U.S.C. 154(b) by 97 days.

(21) Appl. No.: 10/390,733

(22) Filed: Mar. 19, 2003

(65) Prior Publication Data

US 2003/0207790 A1 Nov. 6, 2003

(30) Foreign Application Priority Data

Mar. 22, 2002 (JP) .................................. P.2002-081953

(51) Int. Cl.$^7$ .............................................. A61K 7/46
(52) U.S. Cl. ...................................................... 512/27
(58) Field of Search ........................................... 512/27

(56) References Cited

U.S. PATENT DOCUMENTS

| | | | | |
|---|---|---|---|---|
| 3,956,392 A | * | 5/1976 | DE Haan et al. ............ | 568/376 |
| 4,109,022 A | | 8/1978 | de Haan et al. ............. | 426/538 |
| 4,990,496 A | | 2/1991 | Fehr et al. .................. | 512/24 |
| 5,155,095 A | | 10/1992 | Blanc et al. ................. | 512/21 |
| 5,288,702 A | | 2/1994 | Ogura et al. ................. | 512/24 |
| 6,506,793 B2 | | 1/2003 | Tanaka et al. ............... | 514/463 |
| 2002/0042356 A1 | | 4/2002 | Ujihara et al. .............. | 512/27 |
| 2003/0207789 A1 | | 11/2003 | Yamamoto et al. | |

FOREIGN PATENT DOCUMENTS

| | | |
|---|---|---|
| EP | 1162191 | 12/2001 |
| GB | 1384515 | 2/1975 |
| JP | 4-330033 | 11/1992 |
| JP | 2748184 | 2/1998 |
| JP | 2840899 | 10/1998 |
| JP | 2001-348353 | 12/2001 |

* cited by examiner

Primary Examiner—Jill Warden
Assistant Examiner—Monique T. Cole
(74) Attorney, Agent, or Firm—Fitzpatrick, Cella, Harper & Scinto

(57) ABSTRACT

A geometrical isomer composition excellent in odor and in chemical resistance, which is applicable to a base material containing a strongly alkaline chemical or a strongly acidic chemical, which can suppress the deterioration with time and the color change of the base material in the case that the material is exposed to light, and which also have highly tasteful and unique fruity floral fragrance. A geometrical isomer composition containing 93 to 99% by weight of optically active trans-1-(2,2,6-trimethylcyclohexyl)-2-buten-1-one represented by Formula-1 or a mixture thereof and 7 to 1% by weight of optically active cis-1-(2,2,6-trimethylcyclohexyl)-2-buten-1-one represented by Formula-2 or a mixture thereof is, respectively, used Formula-1

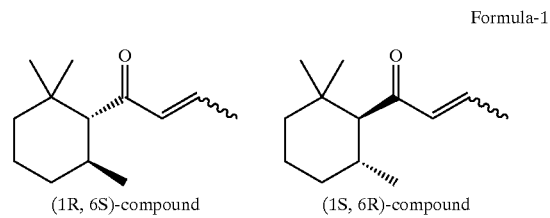

(1R, 6S)-compound   (1S, 6R)-compound

Formula-2

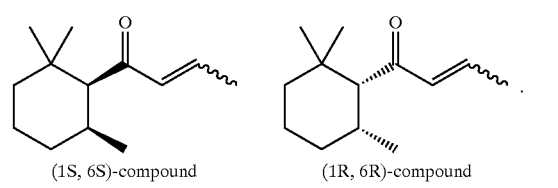

(1S, 6S)-compound   (1R, 6R)-compound

4 Claims, No Drawings

ISOMER COMPOSITION EXCELLENT IN CHEMICAL RESISTANCE CONTAINING OPTICALLY ACTIVE TRANS-1-(2,2,6-TRIMETHYLCYCLOHEXYL)-2-BUTEN-1-ONE AND FRAGRANCE COMPOSITIONS CONTAINING THE ISOMER COMPOSITION

FIELD OF THE INVENTION

The present invention relates to an isomer composition excellent in odor and in chemical resistance containing a geometrical isomer composition containing 93 to 99% by weight of optically active trans-1-(2,2,6-trimethylcyclohexyl)-2-buten-1-one represented by Formula-1 or a mixture thereof and 7 to 1% by weight of optically active cis-1-(2,2,6-trimethylcyclohexyl)-2-buten-1-one represented by Formula-2 or a mixture thereof, respectively, a process for producing the same, and a fragrance composition containing the same.

Formula-1

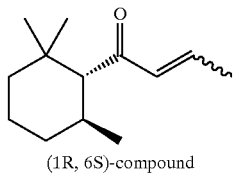
(1R, 6S)-compound

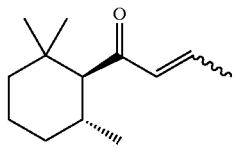
(1S, 6R)-compound

Formula-2

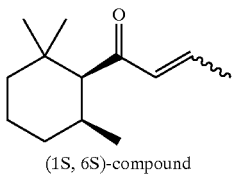
(1S, 6S)-compound

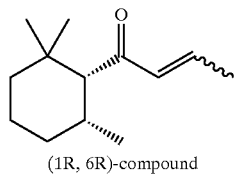
(1R, 6R)-compound

BACKGROUND OF THE INVENTION

In recent years, with regard to fragrance materials, it has been desired to develop a new fragrance material not only having unique and excellent fragrance characteristics but also exhibiting excellent secondary physical properties such as stability to base materials and light stability owing to the increasing diversification of fragrant cosmetics. Particularly, the development of a distinctive fruity floral new fragrance material has been highly requested by fragrances.

During the development of new fragrance materials, the present inventors have found that, when an alkaline material such as soap is mixed with optically active 1-(2,2,6-trimethylcyclohexyl)-2-buten-1-one which is a fruity floral fragrance hitherto widely used, the fragrance of the soap is deteriorated or degraded with time and the color of the soap changes in the case that the soap is exposed to light. In the course of devising a measure to solve these problems, they have noticed that, when a material such as soap is mixed with a geometrical isomer composition containing about 99% by weight of optically active trans-1-(2,2,6-trimethylcyclohexyl)-2-buten-1-one {optical isomer ratio: (1R,6S)-isomer/(1S,6R)-isomer=99/1}, the fragrance of the soap is hardly deteriorated or degraded with time and the color of the soap hardly changes in the case that the soap is exposed to light.

Thus, an object of the invention is to provide a fragrance composition having unique fruity floral fragrance and exhibiting excellent secondary physical properties such as stability to base materials and light stability. Particularly, it is to provide an isomer composition excellent in chemical resistance, which is applicable to a base material containing a strong alkaline chemical or a strong acidic chemical, which can suppress the deterioration or degradation of fragrance with time and the color change of the base material in the case that the material is exposed to light, and which also have highly palatable and unique fruity floral fragrance.

SUMMARY OF THE INVENTION

For the purpose of solving the above problems, the inventors have studied on 1-(2,2,6-trimethylcyclohexyl)-2-buten-1-one including a question of cis/trans ratio. As a result, they have finally accomplished the invention.

Namely, they have found that an isomer composition containing a geometrical isomer composition containing 93 to 99% by weight of optically active trans-1-(2,2,6-trimethylcyclohexyl)-2-buten-1-one represented by Formula-1 or a mixture thereof and 7 to 1% by weight of optically active cis-1-(2,2,6-trimethylcyclohexyl)-2-buten-1-one represented by Formula-2 or a mixture thereof, respectively (hereinafter referred to as an isomer composition of trans-2-buten-1-one having a content of 93 to 99% by weight) exhibits an excellent stability, e.g., a high stability and little deterioration and degradation of fragrance when blended with a base material such as soap and no color change of the soap against light. Moreover, the composition is also stable in a strong alkaline and/or strong acidic material.

Formula-1

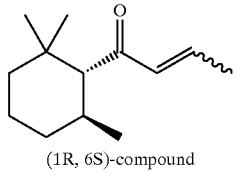
(1R, 6S)-compound

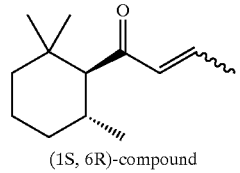
(1S, 6R)-compound

Formula-2

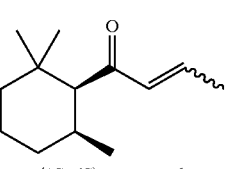
(1S, 6S)-compound

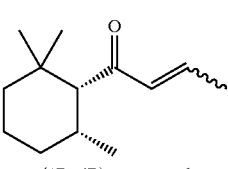
(1R, 6R)-compound

Furthermore, the inventors have found that an isomer composition of trans-2-buten-1-one having a content of 93 to 99% by weight itself and a fragrance composition containing the same acquires totally excellent sensory evaluation and also can be widely used as a fragrance-improving agent in commercial goods in which a strongly basic compound such as ammonia or a very strongly basic compound such as sodium hydroxide or potassium hydroxide is used or commercial goods in which a strongly acidic substance such as hydrochloric acid is used.

Furthermore, it has been revealed that, among the isomer compositions of trans-2-buten-1-one having a content of 93 to 99% by weight, the racemic form, (1S,6R)-isomer, and (1R,6S)-isomer individually exhibit distinctive fruity floral fragrance with regard to fragrance characteristics when blended with a variety of base materials and are excellent in chemical resistance. Namely, it has been found that highly palatable scented products excellent in chemical resistance having distinctive fruity floral fragrance can be provided by utilizing the fragrance characteristics of these racemic form and/or optically active substances depending on the purposes of commercial products.

In this connection, it has been revealed that an isomer composition containing a geometrical isomer composition containing about 91.2% by weight or less of optically active trans-1-(2,2,6-trimethylcyclohexyl)-2-buten-1-one or a mixture thereof and about 8.8% by weight or more of optically active cis-1-(2,2,6-trimethylcyclohexyl)-2-buten-1-one or a mixture thereof is inferior in chemical resistance to strongly alkaline or strongly acidic conditions.

As a result, according to the invention, there are provided an isomer composition excellent in chemical resistance comprising a geometrical isomer composition containing 93 to 99% by weight of optically active trans-1-(2,2,6-trimethylcyclohexyl)-2-buten-1-one represented by Formula-1 or a mixture thereof and 7 to 1% by weight of optically active cis-1-(2,2,6-trimethylcyclohexyl)-2-buten-1-one represented by Formula-2 or a mixture thereof, respectively, a fragrance composition containing the isomer composition, and a fragrance-scented product.

Formula-1

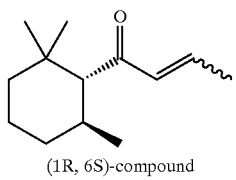  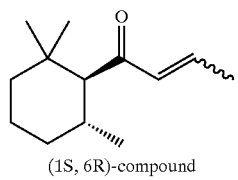

(1R, 6S)-compound    (1S, 6R)-compound

Formula-2

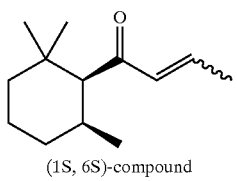  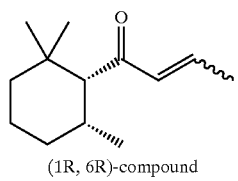

(1S, 6S)-compound    (1R, 6R)-compound

DETAILED DESCRIPTION OF THE INVENTION

The following will explain the present invention in detail.

The above isomer composition excellent in ordor and in chemical resistance may be constituted by only the above geometrical isomer composition or by the geometrical isomer composition and a blending agent commonly used in the fragrance technology field. In some cases, it is also possible to contain compound produced as by-product at the time when the geometrical isomer composition is produced.

As the above geometrical isomer composition, there may be mentioned a geometrical isomer composition containing 93 to 99% by weight of optically active trans-1-(2,2,6-trimethylcyclohexyl)-2-buten-1-one {(1R,6S)-isomer and/or (1S,6R)-isomer} and 7 to 1% by weight of optically active cis-1-(2,2,6-trimethylcyclohexyl)-2-buten-1-one{(1R,6R)-isomer and/or (1S,6S)-isomer}, or a geometrical isomer composition containing 93 to 99% by weight of a mixture of equivalent amount of optically active trans-1-(2,2,6-trimethylcyclohexyl)-2-buten-1-one{(1S,6R)-isomer} and optically active trans-1-(2,2,6-trimethylcyclohexyl)-2-buten-1-one{(1R,6S)-isomer} (racemic form) and 7 to 1% by weight of a mixture of equivalent amount of optically active cis-1-(2,2,6-trimethylcyclohexyl)-2-buten-1-one{(1R,6R)-isomer} and optically active cis-1-(2,2,6-trimethylcyclohexyl)-2-buten-1-one{(1S,6S)-isomer} (racemic form), respectively.

Moreover, the common blending agent to be added to the geometrical isomer composition includes glycols such as glycerin, dipropylene glycol, diethylene glycol, and hexylene glycol; solvents used for common fragrances, such as diethyl phthalate and benzyl benzoate; and the like. It is possible to add basically any amount of the blending agent but the range of the amount to be used is usually from about 20 to 90% by weight on the basis of the geometrical isomer composition.

The following will explain the process for producing the isomer composition excellent in odor and in chemical resistance according to the invention.

As an isomer composition as a synthetic material for the above isomer composition excellent in odor and in chemical resistance, there may be mentioned an isomer composition containing a geometrical isomer composition containing 93 to 99% by weight of optically active trans-2,2,6-trimethylcyclohexyl methyl ketone represented by Formula-3 or a mixture thereof and 7 to 1% by weight of optically active cis-2,2,6-trimethylcyclohexyl methyl ketone represented by Formula-4 or a mixture thereof, respectively (hereinafter referred to as an isomer composition of trans-methyl ketone having a content of 93 to 99% by weight).

Formula-3

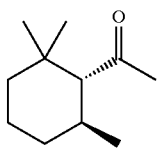  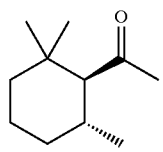

(1R, 6S)-compound    (1S, 6R)-compound

Formula-4

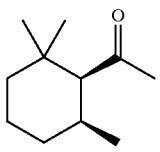  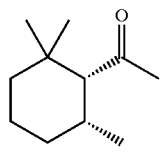

(1S, 6S)-compound    (1R, 6R)-compound

As examples of the geometrical isomer composition which is an essential constitutional component of the above isomer composition, there may be mentioned a geometrical isomer composition containing 93 to 99% by weight of optically active trans-2,2,6-trimethylcyclohexyl methyl ketone represented by Formula-3 {(1R,6S)-isomer and/or (1S,6R)-isomer} and 7 to 1% by weight of optically active cis-2,2,6-trimethylcyclohexyl methyl ketone represented by Formula-4 {(1R,6R)-isomer and/or (1S,6S)-isomer}, respectively, or a geometrical isomer composition containing 93 to 99% by weight of a mixture of equivalent amount of optically active trans-2,2,6-trimethylcyclohexyl methyl ketone{(1S,6R)-isomer} and optically active trans-2,2,6-trimethylcyclohexyl methyl ketone{(1R,6S)-isomer} (racemic form) and 7 to 1% by weight of a mixture of equivalent amount of optically active cis-2,2,6-trimethylcyclohexyl methyl ketone{(1R,6R)-isomer} and optically active cis-2,2,6-trimethylcyclohexyl methyl ketone{(1S,6S)-isomer} (racemic form), respectively.

The isomer composition according to the invention may be constituted by only the above geometrical isomer composition but, in some cases, it is possible to contain a compound produced as by-product at the time when the geometrical isomer composition is produced.

In order to avoid complication, the process for producing the geometrical isomer composition which is an essential constitutional component for the isomer composition of trans-methyl ketone having a content of 93 to 99% by weight will be first explained in the following.

The above geometrical isomer composition can be produced by the method shown in JP-A-2001-348353.

Since no racemization occurs during the production process, the optical purity of the geometrical isomer composition to be prepared according to the above process reflects the optical purity of a starting material to be used.

For example, when (3S)-citronellal or (3R)-citronellal having a high optical purity {an optical purity of 98% e.e. (e.e.: enantiomer excess) in both cases} manufactured by Takasago International Corporation is used as a starting material, a product having a high optical purity (98% e.e.) is obtained. Namely, since the asymmetric carbon atom at the 3-position of the starting material (i.e., (3S) or (3R)) does not directly participate in the reaction and the carbon atom at the 3-position of the starting material corresponds to the carbon atom at the 6-position of the product, the optical purity of the asymmetric carbon atom at 6-position {i.e., (6S) or (6R)} of optically active trans-2,2,6-trimethylcyclohexyl methyl ketone which is a product reflects the optical purity of the asymmetric carbon atom at the 3-position of the starting material, and as a result, optically active trans-2,2,6-trimethylcyclohexyl methyl ketone having an optical purity of 98% e.e. is obtained.

In this connection, the geometrical isomer composition containing 93 to 99% by weight of racemic trans-2,2,6-trimethylcyclohexyl methyl ketone and 7 to 1% by weight of racemic cis-2,2,6-trimethylcyclohexyl methyl ketone can be produced in accordance with the above process. Namely, by carrying out similar operations as in the above process using any one of racemic 7-methoxycitronellal, 7-hydroxycitronellal, and citronellal as a starting material, the geometrical isomer composition containing 93 to 99% by weight of racemic trans-2,2,6-trimethylcyclohexyl methyl ketone and 7 to 1% by weight of racemic cis-2,2,6-trimethylcyclohexyl methyl ketone can be produced.

As a different production process, there may be mentioned a process wherein (1S,6R)-2,2,6-trimethylcyclohexyl methyl ketone which is an optically active trans-isomer and (1R,6S)-2,2,6-trimethylcyclohexyl methyl ketone which is another optically active trans-isomer are separately prepared beforehand and then both compounds are mixed each other to form a mixture of equivalent amount of the (1S,6R)-isomer and the (1R,6S)-isomer (racemic form).

A process based on Japanese Patent No. 2748184 may be mentioned as an alternative synthetic process for the geometrical isomer composition containing 93 to 99% by weight of optically active trans-2,2,6-trimethylcyclohexyl methyl ketone or a mixture thereof and 7 to 1% by weight of optically active cis-2,2,6-trimethylcyclohexyl methyl ketone or a mixture thereof.

Namely, the above composition can be produced using, as a starting material, optically active dihydrocyclocitral containing 90% by weight of its trans-isomer, which is a synthetic intermediate for the production of optically active 1-(2,2,6-trimethylcyclohexyl)-2-buten-1-one, or the racemic dihydrocyclocitral.

More specifically, as shown in Formula-5, by reacting optically active dihydrocyclocitral (1) containing 90% by weight of its trans-isomer with methylmagnesium chloride to obtain a secondary alcohol (2) {the isomer composition ratio of cis-isomer to trans-isomer of the secondary alcohol (2) is the same as the composition of the starting material}, subjecting the secondary alcohol (2) to dehydrogenation in the presence of a copper-chromium catalyst, and carrying out distillation, an optically active trans-2,2,6-trimethylcyclohexyl methyl ketone composition having a trans-isomer content higher than that of the starting alcohol (2) (e.g., 93% by weight of trans-isomer and 7% by weight of cis-isomer) can be produced.

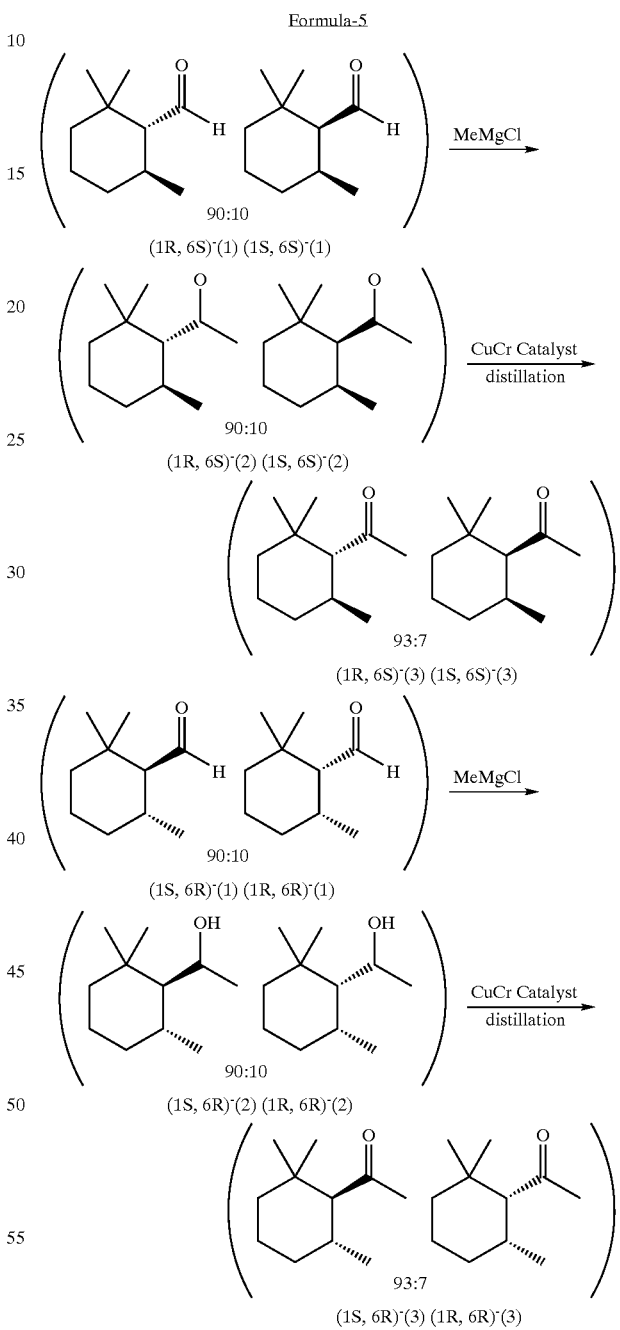

Using the thus synthesized geometrical isomer composition containing 93 to 99% by weight of optically active trans-2,2,6-trimethylcyclohexyl methyl ketone or a mixture thereof and 7 to 1% by weight of optically active cis-2,2,6-trimethylcyclohexyl methyl ketone or a mixture thereof, respectively, as a starting material, a geometrical isomer composition of trans-2-buten-1-one having a content of 93 to 99% by weight can be produced.

The process for producing the above geometrical isomer composition of trans-2-buten-1-one having a content of 93 to 99% by weight is explained, as shown in Formula-6, by illustrating the case that a geometrical isomer composition of optically active trans-2,2,6-trimethylcyclohexyl methyl ketone (3) {trans-isomer/cis-isomer=99/1} is used as a starting material.

Namely, an aldol reagent obtainable from the reaction of an alkylmagnesium bromide (or chloride) represented by ethylmagnesium bromide with N-methylaniline (or the other dialkylamine) is reacted with the above starting ketone composition (3) and the reaction product is further subjected to an addition reaction with acetaldehyde to synthesize an aldol compound (4). Then, by dehydrating the aldol compound (4) using a protonic acid such as p-toluenesulfonic acid (hereinafter referred to as PTS) as a dehydration catalyst, a geometrical isomer composition of optically active 1-(2,2,6-trimethylcyclohexyl)-2-buten-1-one (5) {trans-isomer/cis-isomer={(1R,6S)-(5)/(1S,6S)-(5) and/or (1S,6R)-(5)/(1R,6R)-(5)}={[(1R,6S)-(E)-(5)+(1R,6S)-(Z)-(5)]/[(1S,6S)-(E)-(5)+(1S,6S)-(Z)-(5)] and/or [(1S,6R)-(E)-(5)+(1S,6R)-(Z)-(5)]/[(1R,6R)-(E)-(5)+(1R,6R)-(Z)-(5)]}= 99/1} can be obtained.

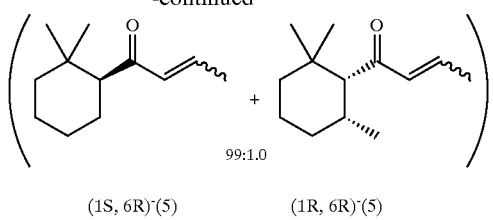

In the above reaction step, i.e., in the case that the dehydration is carried out in the presence of PTS, a product wherein the double bond in the side chain is (E)-form and a product wherein the double bond in the side chain is (Z)-form are formed. The ratio varies depending on the reaction conditions but it has been confirmed that the ratio of (E)-form/(Z)-form is in the range of about (94 to 96)/(6 to 4).

Accordingly, when a geometrical isomer composition of optically active (1R,6S)-2,2,6-trimethylcyclohexyl methyl ketone having a cis-isomer/trans-isomer ratio of 99/1 is used as a starting material in the above process and reacted and then the resulting product is subjected to dehydration using PTS, the values shown in Formula-7 may be generally obtained as the composition ratio of the resulting four kinds of isomers.

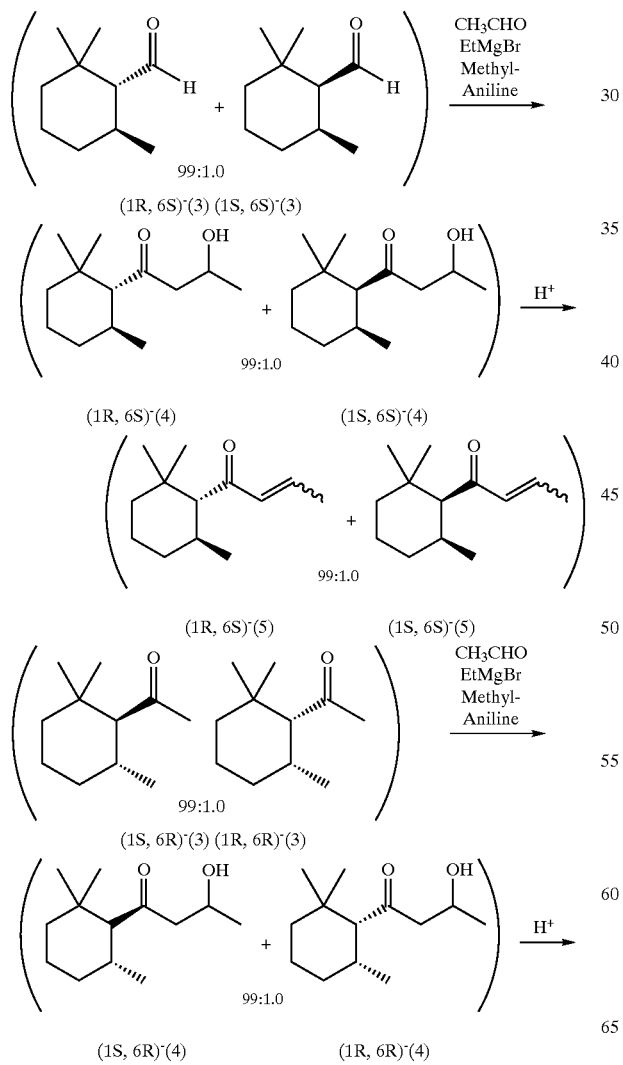

Formula-6

The optical purity of the thus obtained geometrical isomer composition of trans-2-buten-1-one having a content of 93 to 99% by weight means a numerical value calculated according to the following method. Namely, any one asymmetric carbon atom of optically active trans-1-(2,2,6-trimethylcyclohexyl)-2-buten-1-one is focused and an optical purity is determined by applying a usual method to the focused asymmetric carbon atom. For example, in the case of (1R,6S)-1-(2,2,6-trimethylcyclohexyl)-2-buten-1-one which is an optically active trans-isomer, the carbon atom at the 6-position is focused and, when 99% of the carbon atom is S-form and 1% thereof is R-form, the optical purity of the above (1R,6S)-1-(2,2,6-trimethylcyclohexyl)-2-buten-1-one is found to be 98%. In this connection, in the synthesis of 1-(2,2,6-trimethylcyclohexyl)-2-buten-1-one (5) as an aimed compound from the above starting ketone (3), since the optical purity of the starting ketone (3) is maintained, the optical purity of 1-(2,2,6-trimethylcyclohexyl)-2-buten-1-one (5) as an aimed compound reflects the optical purity of the above starting ketone (3).

By adding the above known blending agent to the geometrical isomer composition thus obtained, an isomer composition of trans-2-buten-1-one having a content of 93 to 99% by weight can be produced.

The thus obtained isomer composition of trans-2-buten-1-one having a content of 93 to 99% by weight is excellent in chemical resistance. Namely, the isomer composition is extremely stable even under conditions of a strongly basic compound such as sodium hydroxide, potassium hydroxide, or ammonia (a pH value of about 9 or higher, further about 10 or higher) or a strongly acidic substance such as hydrochloric acid (a pH value of about 4 or lower, further about 3 or lower, still further about 2 or lower). The isomer composition excellent in chemical resistance defined by the invention means an isomer composition which is hardly deteriorated by the above strongly basic compounds or strongly acidic substances and can stably exist for a long period of time. More specifically, as also described in Examples, it exhibits a good stability even in an alkaline base material such as soap, detergent, hairdye, or perm liquid, and is also stable under strongly acidic conditions such as hydrochloric acid. In the case that these base materials are scented with the above geometrical isomer composition, the deterioration of fragrance with time is hardly observed and an excellent and highly tasteful fragrance can be provided. Moreover, as a result of scenting soap and testing its stability to light, it has been surprisingly revealed that the isomer composition of trans-2-buten-1-one having a content of 93 to 99% by weight which is excellent in chemical resistance is hardly colored and satisfies a sufficient condition as fragrance for soap, while damascones (α-damascone, β-damascone, δ-damascone) which are homologs having one double bond in cyclohexane ring of 1-(2,2,6-trimethylcyclohexyl)-2-buten-1-one are remarkably colored and fragrance thereof is also deteriorated.

The thus obtained isomer composition of trans-2-buten-1-one having a content of 93 to 99% by weight which is excellent in chemical resistance is a strongly diffusive, highly tasteful, and unique fragrance-providing agent or fragrance-improving and enhancing agent. Also, as a fragrance component, it can be added to and blended with various fragrant cosmetics, health and hygiene materials, pharmaceuticals, and the like. Namely, product value can be enhanced by blending a suitable amount that is able to provide a unique fragrance to shampoo, body shampoo, rinse, perfume, cologne, hair tonic, hair cream, pomade, other cosmetic base materials for hair growth, face powder, lipstick, other cosmetic base materials and cosmetic cleaners, soap, liquid soap, hairdye, perm liquid, dish washing soap, laundry detergent, softener, room air fresheners, furniture polish, bleach, disinfectant, insecticide, repellent, other various types of health and hygiene cleaners, toothpaste, mouthwash, toilet paper and fragrance-scenting agents for facilitating the taking of pharmaceuticals. Of these, the composition is particularly effective for soap, liquid soap, hairdye, perm liquid, laundry detergent, softener, bleach, disinfectant, insecticide, other various types of health and hygiene cleaners, toothpaste, and mouthwash.

The isomer composition of trans-2-buten-1-one having a content of 93 to 99% by weight which is excellent in chemical resistance can be solely added to and blended with the above commercial products, but it may be mixed with the other fragrance or a conventional blending agent to prepare a new composition and then the composition may be added to the above products.

As the other fragrance, any fragrance can be employed without particular limitation. The conventional blending agent is also not particularly limited.

The blending amount of the above geometrical isomer composition or the composition containing the same in commercial products varies depending on the products and thus is difficult to determine sweepingly, but it can be commonly used in an amount of about 0.001 to 50% by weight, usually 0.01 to 20% by weight.

By using the isomer composition containing of trans-methyl ketone having a content of 93 to 99% by weight as a raw material, an isomer composition of trans-2-buten-1-one having a content of 93 to 99% by weight which is stable to base materials and light and also stable in an alkaline material or acidic material, and which is useful as a floral fruity fragrance can be provided. Moreover, the isomer composition can be also provided at an inexpensive price. Furthermore, a fragrance composition using the isomer composition and a highly tasteful fragrance-scented product using a strongly alkaline and/or strongly acidic material can be also provided.

The following will explain the invention in detail with reference to Examples such as Synthetic Examples, Comparative Examples, and Test Examples, but these Examples are described for the purpose of explanation only and the invention is not limited to these Examples.

SYNTHETIC EXAMPLE-1

Synthesis of Geometrical Isomer Composition Containing 98.6% by Weight of Optically Active trans-2,2,6-trimethylcyclohexyl methyl ketone {Optical Isomer Ratio: (1R,6S)-isomer/(1S,6R)-isomer=99/1}

1—1) Synthesis of (4S)-4,8-dimethyl-7-nonen-2-ol

Magnesium (50 g) and tetrahydrofuran (100 ml) were placed in a 2-liter, 4-necked flask equipped with an intake tube (for methyl chloride), thermometer, condenser and stirrer under a nitrogen stream, followed by heating to 40° C. and adding iodine (one piece) and methyl iodide (1 ml) to activate the magnesium. Then, tetrahydrofuran (600 ml) was added and methyl chloride gas was introduced through the intake tube under stirring. The resulting mixture was then allowed to react at 40 to 45° C. until the magnesium powder disappeared to prepare a solution of methylmagnesium chloride in tetrahydrofuran.

After completion of the reaction, the solution was cooled to room temperature and (3S)-citronellal (290 g: manufactured by Takasago International Corporation, optical purity: 98% e.e.) was added dropwise over a period of 3 hours under cooling with ice. After the dropwise addition, the solution was stirred at the same temperature for 2 hours. After the reaction was completed, the solution was cooled and a solution of water (108 g) in tetrahydrofuran (200 ml) was added dropwise to decompose the unreacted methyl magnesium chloride and the thus produced alkoxide. The formed magnesium chloride hydroxide as a solid was removed through a filter and the resulting solution of the product in tetrahydrofuran was concentrated with an evaporator to obtain a concentrated oil (316 g).

The resulting concentrated oil (316 g) was distilled with a Widmer distiller to obtain 296 g of (4S)-4,8-dimethyl-7-nonen-2-ol (b.p.: 70–71° C./133 Pa).

The purity of the resulting fraction of (4S)-4,8-dimethyl-7-nonen-2-ol on gas chromatography was found to be 99.8% by weight, and spectral data indicated the values shown below.

GC/MS (m/e); 170 (M⁺, 10%), 152 (2), 137 (8), 109 (70), 95 (65), 82 (100), 69 (80), 55 (50), 43 (76) IR (NaCl); 3343 cm⁻¹ (br) NMR [δ (CDCl₃)]; 5.10 (t, 1H, J=7.1 Hz), 3.89 (dq 1H, J=12.8, 6.2 Hz), 2.0 (m, 2H), 1.68 (s, 3H), 1.60 (s, 3H), 1.55 (m, 1H), 1.5 (m, 1H), 1.4 (m, 2H), 1.19 (d, 3H, J=6.2 Hz), 1.1 (m, 1H), 0.91 (d, 3H, J=6.6 Hz)

1-2) Synthesis of (4S)-4,8-dimethyl-7-nonen-2-one

Acetone (2,000 ml) and (4S)-4,8-dimethyl-7-nonen-2-ol (240 g) synthesized in Synthetic Example 1—1 were placed in a 5-liter, 4-necked flask equipped with a dropping funnel, thermometer, condenser, and stirrer. Jones reagent {prepared from water (520 ml), concentrated sulfuric acid (165 g), and chromium trioxide (112 g)} placed in the dropping funnel was added dropwise over a period of 4 hours under cooling with ice. After the dropwise addition, the mixture was stirred for 2 hours. Then, sodium hydrogen sulfite was added gradually until the orange color of chromium (VI) disappeared. The liquid was then separated and the bottom layer was extracted with petroleum ether (1,000 ml). Since the liquid again separated into two layers when the extract was combined with the previous upper layer, the lower layer was added to the previous lower layer and further extracted three times with 500 ml of petroleum ether. After combining the petroleum ether layers and washing with a saturated brine, a saturated aqueous sodium hydrogen carbonate solution and again with a saturated brine, the solvent was evaporated. The resulting concentrated oil was distilled with a Widmer distiller to obtain 194 g of (4S)-4,8-dimethyl-7-nonen-2-one (b.p.: 63° C./133 Pa).

The purity of the resulting fraction on gas chromatography was found to be 99.5% by weight, and spectral data indicated the values shown below.

GC/MS (m/e) ; 168 (M⁺, 19%), 150 (8), 135 (25), 110 (58), 95 (100), 85 (42), 69 (47), 43 (64) IR (NaCl); 1716 cm⁻¹ NMR [δ (CDCl₃)]; 5.09 (t, 1H, J=7.1 Hz), 2.42 (dd, 1H, J=5.6, 15.7 Hz), 2.22 (dd, 1H, J=8.2, 15.7 Hz), 2.0 (m, 1×3H), 1.68 (s, 3H), 1.60 (s, 3H), 1.3 (m, 1H), 1.2 (m, 1H), 0.91 (d, 3H, J=6.6 Hz)

1-3) Synthesis of (4S)-4,8-dimethyl-2,7-(and -1,7-)-nonadien-2-yl acetate Composition Under a nitrogen stream, (4S)-4,8-dimethyl-7-nonen-2-one (168 g) synthesized in Synthetic Example 1-2, isopropenyl acetate (200 g), and p-toluenesulfonic acid monohydrate (19 g) were placed in a 3,000 ml, 4-necked flask equipped with a thermometer, condenser, and stirrer, followed by reaction at 90° C. for 22 hours under stirring. As a result of sampling the product and analyzing it by gas chromatography, it was confirmed by the mass spectral data shown below that three types of (4S)-4,8-dimethyl-2,7-(and 1,7)-nonadien-2-yl acetate: (4S)-(6) {area composition by gas chromatography: (4S)-(6–1), 50.3%; (4S)-(6–2), 16.4%; (4S)-(6–3) 26.8%} were formed.

The products were subjected to a subsequent cyclization reaction without further treatment. Mass spectra of three types of (4S)-4,8-dimethyl-2,7- (and 1,7)-nonadien-2-yl acetate (4S)-[6–1]; 210 (M⁺, 1%), 168 (17), 150 (68), 135 (38), 109 (77), 95 (57), 85 (100), 69 (47), 43 (100)
(4S)-[6–2]; 210 (M⁺, 1%), 168 (10), 150 (57), 135 (30), 109 (68), 95 (43), 85 (98), 69 (36), 43 (100)
(4S)-[6–3]; 210 (M⁺, 1%), 167 (8), 150 (64), 135 (38), 109 (100), 95 (75), 85 (30), 69 (62), 43 (94)

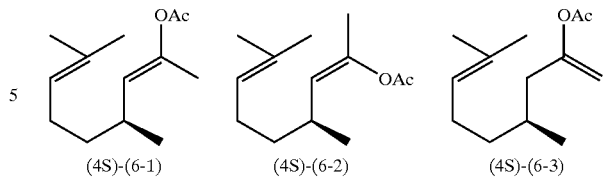

(4S)-(6-1)    (4S)-(6-2)    (4S)-(6-3)

IR and NMR spectra of a mixture of three types of (4S)-4,8-dimethyl-2,7-(and 1,7)-nonadien-2-yl acetate IR (NaCl); 1756 cm⁻¹, 1213 cm⁻¹ NMR [δ (CDCl₃)]; 5.06 (t, 1H), 4.74 (t, 1H, 10.6 Hz), 2.11 (s, 3H), 2.0 (m, 2H), 1.66 (s, 3H), 1.58 (s, 3H), 1.1 (m, 2H), 1.0 (m, 1H), 0.91 (d, 3H)

1-4) Synthesis of Geometrical Isomer Composition Containing 98.6% by Weight of Optically Active trans-2,2,6-trimethylcyclohexyl methyl ketone {Optical Isomer Ratio: (1R,6S)-isomer/(1S,6R)-isomer=99/1}

85% by weight phosphoric acid (50 g) and toluene (1,500 ml) were added to a reaction liquid containing three types of (4S)-4,8-dimethyl-2,7-(and 1,7)-nonadien-2-yl acetate synthesized in Synthetic Example 1–3 and the resulting mixture was reacted at 100° C. for 32 hours. After cooling the reaction liquid, the liquid was washed with water, a saturated aqueous sodium carbonate solution, and a saturated brine and then the solvent was evaporated. The resulting concentrated oil (area composition on gas chromatography: trans-isomer=64.5%, cis-isomer=1.1%, and small amounts of other unknown components=34.4%) was purified with a 50-stage precision distiller to obtain a geometrical isomer composition of optically active trans-2,2,6-trimethylcyclohexyl methyl ketone {optical isomer ratio: (1R,6S)-isomer/(1S,6R)-isomer=99/1} (area ratio on gas chromatography: trans-isomer/cis-isomer=98.6/1.4, b.p.: 78° C./1197 Pa, [α]_D^{24}=−23.80° (c=1.00, EtOH, 24° C.)).

The resulting fraction demonstrated spectral data having the values shown below.

GC/MS (m/e) ; 168 (M⁺, 34%), 153 (10), 135 (17), 125 (20), 110 (62), 99 (100), 85 (45), 69 (89), 43 (62) IR (NaCl); 1708 cm⁻¹ NMR [δ (CDCl₃)]; 2.16 (s, 3H), 2.07 (d, 1H, J=11.2 Hz), 1.8 (m, 1H), 1.7 (dq, 1H), 1.5 (m, 2H), 1.4 (ddd, 1H, J=1.4, 3.3, 13.1 Hz), 1.2 (m, 1H), 0.96 (s, 3H), 0.93 (s, 3H), 0.9 (m, 1H), 0.81 (d, 3H, J=6.3 Hz)

SYNTHETIC EXAMPLE-2

Synthesis of Geometrical Isomer Composition Containing 98.5% by Weight of Optically Active trans-2,2,6-trimethylcyclohexyl methyl ketone {Optical Isomer Ratio: (1S,6R)-isomer/(1R,6S)-isomer=99/1}

Using (3R)-citronellal (manufactured by Takasago International Corporation; optical purity: 98% e.e.) as a starting material, the reaction was carried out in exactly the same manner as the synthetic operations in Synthetic Example-1 to obtain 73 g of a geometrical isomer composition of trans-2,2,6-trimethylcyclohexyl methyl ketone {optical isomer ratio: (1S,6R)-isomer/(1R,65)-isomer=99/1} {b.p.: 78° C./1197 Pa, [α]_D^{24}=+23.98° (c=1.00, EtOH, 24° C.), area ratio on gas chromatography: trans-isomer/cis-isomer=98.5/1.5}.

SYNTHETIC EXAMPLE-3

Synthesis of Geometrical Isomer Composition Containing 99% by Weight of Racemic trans-2,2,6-trimethylcyclohexyl methyl ketone Using racemic citronellal as a starting material, the reaction was carried out in exactly the same manner as the synthetic operations in Synthetic Example-1 to obtain 73 g of racemic trans-2,2,6-trimethylcyclohexyl methyl ketone (b.p.: 78° C./1197 Pa, area ratio on gas chromatography: trans-isomer/cis-isomer=99/1).

SYNTHETIC EXAMPLE-4

Synthesis of Geometrical Isomer Composition Containing 93% by Weight of Optically Active trans-2,2,6-trimethylcyclohexyl methyl ketone {Optical Isomer Ratio: (1R,6S) -isomer/(1S,6R)-isomer=99/1}

4-1) Synthesis of Geometrical Isomer Composition Containing 90% by Weight of Optically Active trans-1-(2,2,6-trimethylcyclohexyl)ethan-1-ol {Optical Isomer Ratio: (1R, 6S)-isomer/(1S,6R)-isomer=99/1}

Using a geometrical isomer composition (154 g) containing, as a main component, optically active trans-2,2,6-trimethylcyclohexylcarbaldehyde {optical isomer ratio: (1R,6S)-isomer/(1S,6R)-isomer=99/1} produced in accordance with the method of Example-2 of Japanese patent No. 2840899 (area ratio on gas chromatography: trans/cis=90/10), a reaction with methylmagnesium chloride was carried out in the same manner as the method described in Synthetic Example 1—1 to obtain 146 g of a geometrical isomer composition of optically active trans-1-(2,2,6-trimethylcyclohexyl)ethan-1-ol {optical isomer ratio: (1R, 6S)-isomer/(1S,6R)-isomer=99/1} (b.p.: 60° C./33.2 Pa, $[\alpha]_D^{24}$=-14.71° (c=1.00, EtOH, 24° C.), area ratio on gas chromatography: trans-isomer/cis-isomer =90/10).

The spectral data indicated the values shown below.

GC/MS (m/e); 170 (M$^+$, 0%), 152 (1), 137 (10), 125 (45), 111 (92), 95 (19), 83 (70), 69 (100), 55 (60), 41 (49) IR (NaCl); 3442 cm$^{-1}$ (br) NMR [δ (CDCl$_3$)]; 4.14 (q, 1H, J=6.9 Hz), 1.7 (m, 1H), 1.4 (m, 2H), 1.3 (m, 1H), 1.30 (d, 3H, 6.9 Hz), 1.2 (m, 1H), 1.15 (d, 3H, J=7.3 Hz), 1.1 (m, 1H), 1.0 (m, 1H), 0.91 (s, 3H), 0.90 (s, 3H), 0.81 (d, 1H, J=10.9 Hz)

4-2) Synthesis of Geometrical Isomer Composition Containing 93% by Weight of Optically Active trans-2,2,6-trimethylcyclohexyl methyl ketone {Optical Isomer Ratio: (1R,6S)-isomer/(1S,6R)-isomer=99/1}

The geometrical isomer composition (100 g) containing 90% by weight of optically active trans-1-(2,2,6-trimethylcyclohexyl)ethan-1-ol synthesized in Synthetic Example 4-1 and a copper-chromium catalyst (5 g) pre-activated with hydrogen were placed in a 200 ml autoclave, followed by reaction at 200° C. for 6 hours. After cooling the reaction mixture and removing the catalyst by filtration, the reaction liquid was distilled with a Widmer distiller to obtain 89 g of a composition having an increased trans-isomer content by 3% by weight through the reaction as compared with the content in the starting material, i.e., a geometrical isomer composition containing 93% by weight of optically active trans-2,2,6-trimethylcyclohexyl methyl ketone {optical isomer ratio: (1R,6S)-isomer/(1S,6R)-isomer=99/1} {area ratio on gas chromatography: trans-isomer/cis-isomer=93/7, $[\alpha]_D^{24}$=-21.92° (c=1.00, EtOH, 24° C.), b.p.: 76–78° C./1197 Pa}.

SYNTHETIC EXAMPLE-5

Synthesis of Geometrical Isomer Composition of Racemic 2,2,6-trimethylcyclohexyl methyl ketone (trans-isomer/cis-isomer=93.0/7.0)

A reaction was carried out in exactly the same manner as in Synthetic Example 4 with the exception that 2,2,6-trimethylcyclohexylcarbaldehyde containing trans-isomer as a main component (area ratio on gas chromatography: trans-isomer/cis-isomer=90/10) synthesized by the method described in Example-2 of Japanese patent No. 2840899 using racemic citranellol was used instead of optically active trans-2,2,6-trimethylcyclohexylcarbaldehyde (area ratio on gas chromatography: trans-isomer/cis-isomer=90/10) used as a starting material in Synthetic Example-4, whereby 89 g of a geometrical isomer composition containing 93% by weight of racemic trans-2,2,6-trimethylcyclohexyl methyl ketone (area ratio on gas chromatography: trans-isomer/cis-isomer=93/7; b.p.: 76–78° C./1197 Pa) was obtained.

SYNTHETIC EXAMPLE-6

Synthesis of Geometrical Isomer Composition Containing 93% by Weight of Optically Active trans-2,2,6-trimethylcyclohexyl methyl ketone {Optical Isomer Ratio: (1S,6R)-isomer/(1R,6S)-isomer=99/1}

A reaction was carried out in exactly the same manner as in Synthetic Example-4 with the exception that optically active trans-2,2,6-trimethylcyclohexylcarbaldehyde containing trans-isomer as a main component (optical isomer ratio: (1S,6R)-isomer/(1R,6S)-isomer=99/1, area ratio on gas chromatography: trans-isomer/cis-isomer=(1R,6S)/(1S,6S)=90/10) synthesized by the method described in Example-2 of Japanese patent No. 2840899 using (3R)-citronellal was used instead of 2,2,6-trimethylcyclohexylcarbaldehyde (area ratio on gas chromatography: trans-isomer/cis-isomer=90/10) used as a starting material in Synthetic Example-4, whereby 89 g of a geometrical isomer composition containing 93% by weight of optically active trans-2,2,6-trimethylcyclohexyl methyl ketone {optical isomer ratio: (1S,6R)-isomer/(1R,6S)-isomer=99/1; area ratio on gas chromatography: trans-isomer/cis-isomer=93/7; $[\alpha]_D^{24}$=+21.90° (c=1.00, EtOH, 24° C.), b.p.: 76–78° C./1197 Pa} was obtained.

SYNTHETIC EXAMPLE-7

Synthesis of Geometrical Isomer Composition Containing 98.7% by Weight of Optically Active trans-1-(2,2,6-trimethylcyclohexyl)-2-buten-1-one {Optical Isomer Ratio: (1R,6S)-isomer/(1S,6R)-isomer=99/1}

Under ice-cooling and stirring, a solution containing N-methylaniline (23.8 g) dissolved in 70 ml of toluene was added to a tetrahydrofuran solution (82 ml) of ethyl magnesium bromide, produced in 60 ml of tetrahydrofuran from ethyl bromide (30.0 g) and magnesium (5.9 g) in a 500 ml, 4-necked flask equipped with a thermometer, condenser, and stirrer under a nitrogen stream. While maintaining this freshly prepared methylaniline-magnesium bromide solution at a temperature of 0° C., a toluene (37 ml) solution of the geometrical isomer composition (37 g) of optically active 2,2,6-trimethylcyclohexyl methyl ketone synthesized in Synthetic Example-1 was added dropwise over a period of 30 minutes, followed by additional stirring at the same temperature for 30 minutes.

Next, a solution of acetaldehyde (14.6 g) in toluene (15 ml) was added dropwise over a period of 30 minutes at −10 to −15° C. After completion of the dropwise addition, the mixture was additionally stirred for 90 minutes to complete the reaction. Then, 3 N hydrochloric acid (150 ml) was added to the reaction liquid under stirring and cooling with ice to conduct decomposition, and then the mixture was washed with water, and subjected to liquid separation. The resulting organic layer was washed five times with 100 ml of 3 N hydrochloric acid and separated. After p-toluenesulfonic acid (0.5 g) was added to a toluene solution of the resulting aldol compound {4-(2,6,6-trimethylcyclohexyl)-4-oxo-butan-2-ol} and the mixture was heated, the water formed through the dehydration reaction was separated under reflux with toluene to complete the dehydration reaction. After 50 ml of water was added to the cooled reaction liquid and the mixture was washed and subjected to liquid separation, the liquid was washed with 50 ml of aqueous sodium bicarbonate solution and 50 ml of water and separated. Then, the resulting organic layer was concentrated with an evaporator to obtain 42 g of a concentrated oil. This oil was then distilled with a Widmer distiller to obtain 28 g of a geometrical isomer composition of optically active 1-(2,2,6-trimethylcyclohexyl)-2-buten-1-one composed of four types of geometrical isomers as shown in Formula-8: {optical isomer ratio: (1R,6S)-isomer/(1S,6R)-isomer=99/1, area ratio on gas chromatography: trans-isomer/cis-isomer={trans-(E)-isomer+trans-(Z)-isomer}/{cis-(E)-isomer+cis-(Z)-isomer}=(92.9+5.8)/(1.2+0.1)=98.7/1.3; b.p.: 73–75° C./20 Pa, $[\alpha]_D^{24}$=−15.52° (c=1.00, EtOH, 24° C.)}.

This fraction had excellent fragrance characteristics.

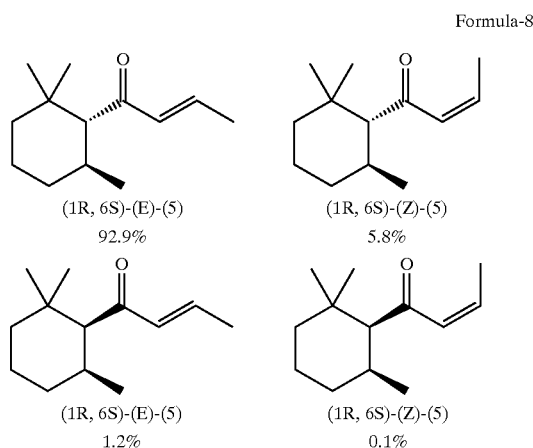

Formula-8

(1R, 6S)-(E)-(5)
92.9%

(1R, 6S)-(Z)-(5)
5.8%

(1R, 6S)-(E)-(5)
1.2%

(1R, 6S)-(Z)-(5)
0.1%

SYNTHETIC EXAMPLE-8

Synthesis of Geometrical Isomer Composition Containing 99% by Weight of Optically Active trans-1-(2,2,6-trimethylcyclohexyl)-2-buten-1-one {Optical Isomer Ratio: (1S,6R)-isomer/(1R,6S)-isomer=99/1}

A reaction was carried out in exactly the same manner as in Synthetic Example-7 using 37 g of the geometrical isomer composition of optically active 2,2,6-trimethylcyclohexyl methyl ketone synthesized in Synthetic Example-2. The resulting crude product was separated by rectification to obtain 29 g of a geometrical isomer composition of optically active 1-(2,2,6-trimethylcyclohexyl)-2-buten-1-one {optical isomer ratio: (1S,6R)-isomer/(1R,6S)-isomer=99/1} composed of four types of geometrical isomers shown in Formula-9: {area ratio on gas chromatography: trans-isomer/cis-isomer={trans-(E)-isomer+trans-(Z)-isomer}/{cis-(E)-isomer+cis-(Z)-isomer}=(93.1+5.9)/(1.0+0.1)=99.0/1.1; b.p. 73–75° C./20 Pa, $[\alpha]_D^{24}$=+16.10° (c=1.00, EtOH, 24° C.)}.

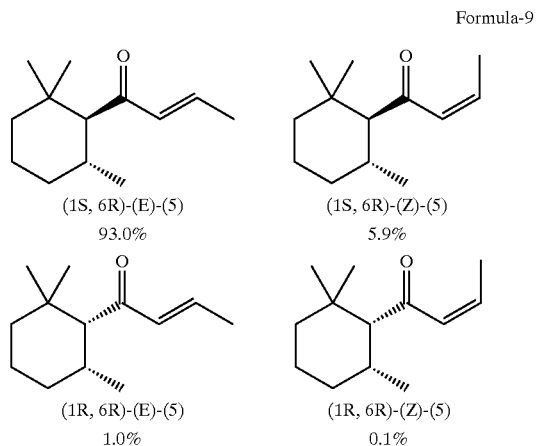

Formula-9

(1S, 6R)-(E)-(5)
93.0%

(1S, 6R)-(Z)-(5)
5.9%

(1R, 6R)-(E)-(5)
1.0%

(1R, 6R)-(Z)-(5)
0.1%

SYNTHETIC EXAMPLE-9

Synthesis of Geometrical Isomer Composition of Racemic 1-(2,2,6-trimethylcyclohexyl)-2-buten-1-one {trans-isomer/cis-isomer=99.0/1.0}

A reaction was carried out in exactly the same manner as in Synthetic Example-7 using 37 g of the geometrical isomer composition of racemic 2,2,6-trimethylcyclohexyl methyl ketone {trans-isomer/cis-isomer=99/1} synthesized in Synthetic Example-3 to obtain 29 g of a geometrical isomer composition of racemic 1-(2,2,6-trimethylcyclohexyl)-2-buten-1-one {trans-isomer/cis-isomer=99/1}: {b.p.: 73–75° C./20 Pa}. The geometrical isomer composition indicated the composition values of four types of geometrical isomers as shown in Formula-10 on gas chromatography. Namely, the composition values of trans-isomer/cis-isomer={trans-(E)-isomer+trans-(Z)-isomer}/{cis-(E)-isomer+cis-(Z)-isomer}=(93.0+5.9)/(0.9+0.1)=99.0/1.0 were found.

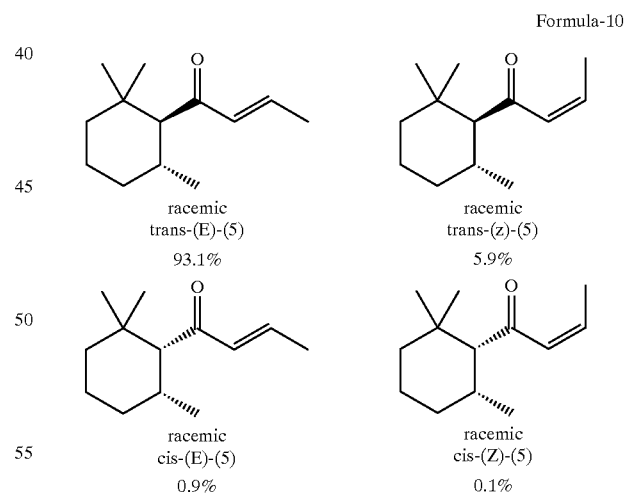

Formula-10 racemic
trans-(E)-(5)
93.1% racemic
trans-(z)-(5)
5.9% racemic
cis-(E)-(5)
0.9% racemic
cis-(Z)-(5)
0.1%

SYNTHETIC EXAMPLE-10

Synthesis of Geometrical Isomer Composition Containing 93% by Weight of Optically Active trans-1-(2,2,6-trimethylcyclohexyl)-2-buten-1-one {Optical Isomer Ratio: (1R,6S)-isomer/(1S,6R)-isomer=99/1}

A reaction was carried out in exactly the same manner as in Synthetic Example-7 using 37 g of the geometrical isomer composition containing 93% by weight of optically active trans-2,2,6-trimethylcyclohexyl methyl ketone {optical isomer ratio: (1R,6S)-isomer/(1S,6R)-isomer=99/1} synthesized in Synthetic Example-4 to obtain 29 g of a geometrical isomer composition of optically active 1-(2,2,6-trimethylcyclohexyl)-2-buten-1-one {optical isomer ratio: (1R,6S)-isomer/(1S,6R)-isomer=99/1}: {b.p.: 73–75° C./20 Pa, $[\alpha]_D^{24}$=−14.83° (c=1.00, EtOH, 24° C.)}. The geometrical isomer composition indicated the composition values of four types of geometrical isomers as shown in Formula-11 on gas chromatography. Namely, the composition values of trans-isomer/cis-isomer={trans-(E)-isomer+trans-(Z)-isomer}/{cis-(E)-isomer+cis-(Z)-isomer}=(88.9++4.1)/(6.7+0.3)=93/7 were found.

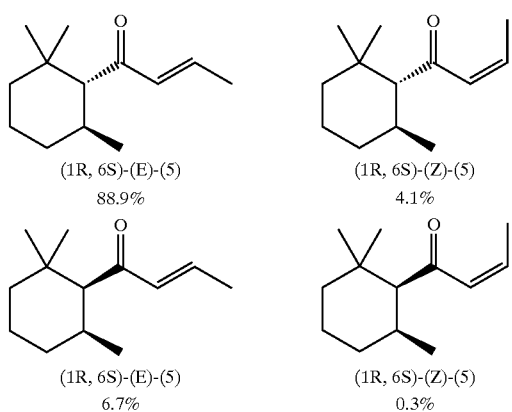

Formula-11

SYNTHETIC EXAMPLE-11

Synthesis of Geometrical Isomer Composition Containing 93.1% by Weight of Optically Active trans-1-(2,2,6-trimethylcyclohexyl)-2-buten-1-one {Optical Isomer Ratio: (1S,6R)-isomer/(1R,6S)-isomer=99/1}

A reaction was carried out in exactly the same manner as in Synthetic Example-7 using 37 g of the geometrical isomer composition containing 93% by weight of 2,2,6-trimethylcyclohexyl methyl ketone {optical isomer ratio: (1S,6R)-isomer/(1R,6S)-isomer=99/1} synthesized in Synthetic Example-6 to obtain 29 g of a geometrical isomer composition of optically active 1-(2,2,6-trimethylcyclohexyl)-2-buten-1-one {optical isomer ratio: (1S,6R)-isomer/(1R,6S)-isomer=99/1}: {b.p.: 73–75° C./20 Pa, $[\alpha]_D^{24}$=°14.80° (c=1.00, EtOH, 24° C.)}. The geometrical isomer composition indicated the composition values of four types of geometrical isomers as shown in Formula-12 on gas chromatography. Namely, the composition values of trans-isomer/cis-isomer={trans-(E)-isomer+trans-(Z)-isomer}/{cis-(E)-isomer+cis-(Z)-isomer}=(89.0+4.1)/(6.6+0.3)=93.1/6.9 were found.

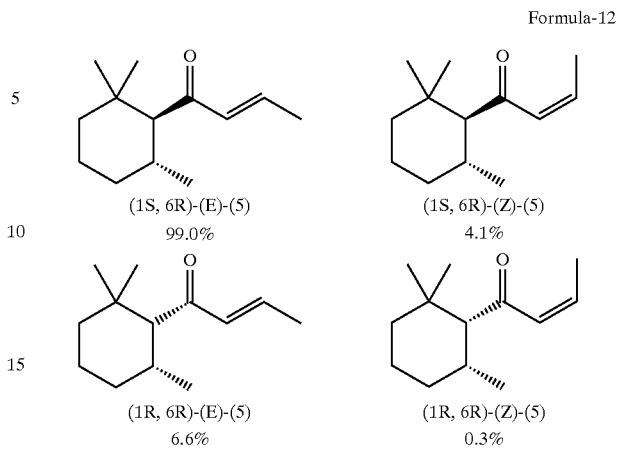

Formula-12

SYNTHETIC EXAMPLE-12

Synthesis of Geometrical Isomer Composition of Racemic 1-(2,2,6-trimethylcyclohexyl)-2-buten-1-one(trans-isomer/cis-isomer=93.0/7.0)

A reaction was carried out in exactly the same manner as in Synthetic Example-7 using 37 g of racemic 2,2,6-trimethylcyclohexyl methyl ketone (trans-isomer/cis-isomer=93/7) synthesized in Synthetic Example-5 to obtain 29 g of a geometrical isomer composition of racemic 1-(2,2,6-trimethylcyclohexyl)-2-buten-1-one: {b.p.: 73–75° C./20 Pa). The geometrical isomer composition indicated the composition values of four types of geometrical isomers as shown in Formula-13 on gas chromatography. Namely, the composition values of trans-isomer/cis-isomer=trans-(E)-isomer+trans-(Z)-isomer}/{cis-(E)-isomer+cis-(Z)-isomer}=(89.0+4.0)/(6.7+0.3)=93.0/7.0 were found.

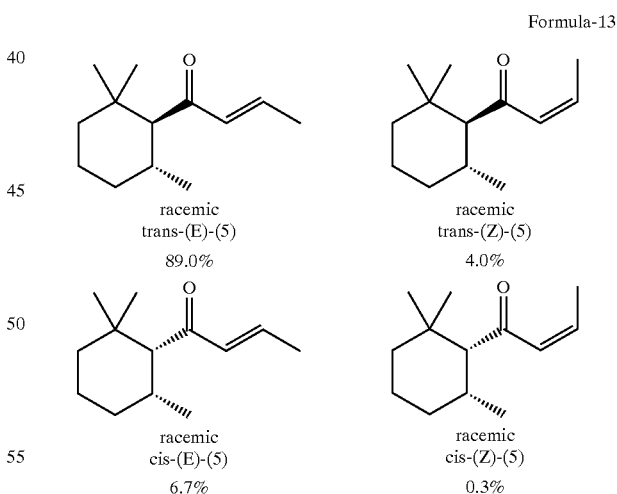

Formula-13

COMPARATIVE EXAMPLE-1

Synthesis of Geometrical Isomer Composition Containing 91.2% by weight of Optically Active trans-1-(2,2,6-trimethylcyclohexyl)-2-buten-1-one {Optical Isomer Ratio: (1R,6S)-isomer/(1S,6R)-isomer=99/1}

A reaction was carried out in exactly the same manner as in Example-1 of Japanese Patent No. 2748184 relating to the present inventors to obtain 30 g of a geometrical isomer composition of optically active 1-(2,2,6-trimethylcyclohexyl)-2-buten-1-one{optical isomer ratio: (1R,6S)-isomer/(1S,6R)-isomer=99/1} containing (1R,6S)-(E)-(5) as a main component: {b.p.: 67–69° C./40 Pa, $[\alpha]_D^{24}$=−12.560 (c=1.00, EtOH, 24° C.)}. The geometrical isomer composition indicated the composition values of four types of geometrical isomers as shown in Formula-14 on gas chromatography. Namely, the composition values of trans-isomer/cis-isomer={trans-(E)-isomer+trans-(Z)-isomer}/{cis-(E)-isomer+cis-(Z)-isomer}=(87.2+4)/(8.4+0.3)=91.2/8.7 were found.

Formula-14

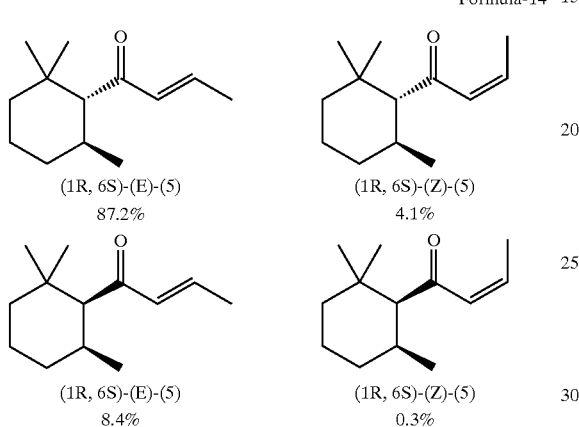

(1R, 6S)-(E)-(5)
87.2%

(1R, 6S)-(Z)-(5)
4.1%

(1R, 6S)-(E)-(5)
8.4%

(1R, 6S)-(Z)-(5)
0.3%

COMPARATIVE EXAMPLE-2

Synthesis of Geometrical Isomer Composition Containing 91.2% by weight of optically active trans-1-(2,2,6-trimethylcyclohexyl)-2-buten-1-one {optical isomer ratio: (1S,6R)-isomer/(1R,6S)-isomer=99/1}

As in Synthetic Example 13, a reaction was carried out in exactly the same manner as in Example-2 of Japanese Patent No. 2748184 to obtain 29 g of a geometrical isomer composition of optically active 1-(2,2,6-trimethylcyclohexyl)-2-buten-1-one {optical isomer ratio: (1S,6R)-isomer/(1R,6S)-isomer=99/1} containing (1S,6R)-(E)-(5) as a main component: {b.p.: 67–69° C./40 Pa, $[\alpha]_D^{24}$=−12.53° (c=1.00, EtOH, 24° C.)}. The geometrical isomer composition indicated the composition values as shown in Formula-15 on gas chromatography. Namely, the composition values of trans-isomer/cis-isomer={trans-(E)-isomer+trans-(Z)-isomer}/{cis-(E)-isomer+cis-(Z)-isomer}=(87.1+4.1)/(8.5+0.3)=91.2/8.8 were found.

Formula-15

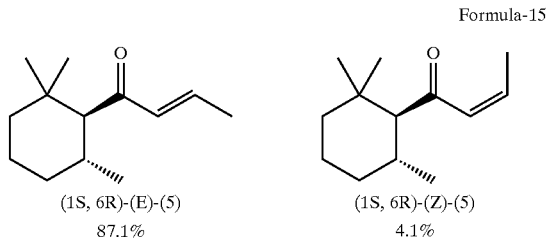

(1S, 6R)-(E)-(5)
87.1%

(1S, 6R)-(Z)-(5)
4.1%

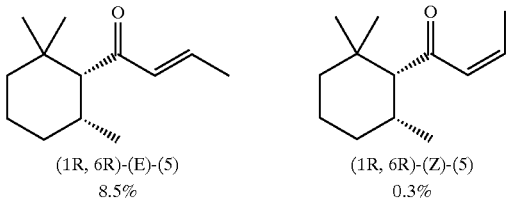

(1R, 6R)-(E)-(5)
8.5%

(1R, 6R)-(Z)-(5)
0.3%

COMPARATIVE EXAMPLE-3

Synthesis of Geometrical Isomer Composition of Racemic 1-(2,2,6-trimethylcyclohexyl)-2-buten-1-one(trans-isomer/cis-isomer=91.2/8.8)

A reaction was carried out in exactly the same manner as in Example-1 of Japanese Patent No. 2748184 with the exception that racemic citronellal was used as a starting material, whereby 29 g of a geometrical isomer composition of 1-(2,2,6-trimethylcyclohexyl)-2-buten-1-one containing racemic trans-(E)-(5) as a main component: {b.p.: 67–69° C./40 Pa}. The geometrical isomer composition indicated the composition values as shown in Formula-16 on gas chromatography. Namely, the composition values of trans-isomer/cis-isomer={trans-(E)-isomer+trans-(Z)-isomer}/{cis-(E)-isomer+cis-(Z)-isomer}=(87.1+4.1)/(8.6+0.2)=91.2/8.8 were found.

Formula-16

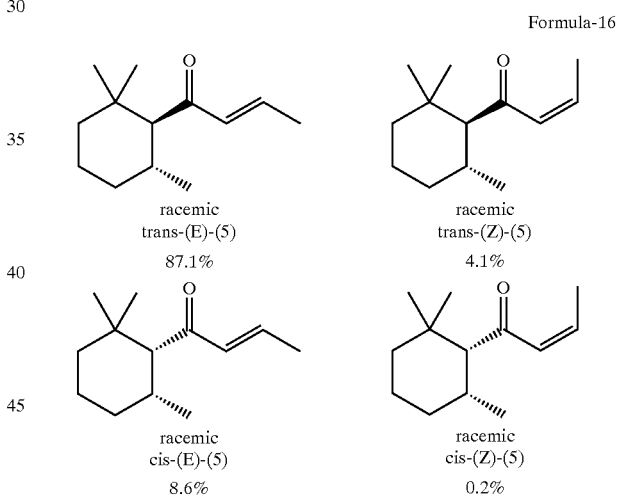

racemic trans-(E)-(5)
87.1% racemic trans-(Z)-(5)
4.1% racemic cis-(E)-(5)
8.6% racemic cis-(Z)-(5)
0.2%

TEST EXAMPLE-1

Scenting and Stability Test of 1-(2,2,6-trimethylcyclohexyl)-2-buten-1-one in Soap, and Soap Fragrance Composition using the Same Stability of a fragrance to a soap base material when the soap is scented therewith frequently varies depending on kind of the base material, influence of minute amount of impurity in a treatment, and the like.

In the present test, using a soap base material (sodium salt of a mixture of 20% by weight of palm and 80% by weight of beef tallow) which was one of representative base materials, scented soaps were obtained by scenting the soap base material with 1% by weight of each of the geometrical isomer compositions of 1-(2,2,6-trimethylcyclohexyl)-2-buten-1-one (5) synthesized in Synthetic Examples and also a blank soap was prepared. The scented soaps were each placed in a glass vessel, which was then tightly closed. After the vessel was stored in a constant temperature chamber at 40° C. for a certain period of time (1 month or 3 months), change of the fragrance was investigated by three expert panelists. As another test, change of suntan when the soaps were exposed to sunlight (after 1 month) was tested on six samples having different cis/trans ratios.

The results are shown in Table-1.

In this connection, the symbols in the table are as follows.

Fragrance Quality
⊚⊚ absolutely no change
⊚○ almost no change
○○ presence of slight decomposition smell
○Δ weak fragrance and presence of decomposition smell
ΔX strong decomposition smell
XX remarkable deterioration of fragrance and presence of decomposition smell Suntan
⊚ the same as blank
○ about the same as blank
Δ A slightly colored
X colored into dark brown sition containing 93 to 99% by weight of racemic and/or optically active trans-1-(2,2,6-trimethylcyclohexyl)-2-buten-1-one{optical isomer ratio; (1S,6R)-isomer/(1R,6S)-isomer=99/1 or 1/99} is extremely useful as a fragrance having fruity floral fragrance.

TEST EXAMPLE-2

Masking and Stability Test using 1-(2,2,6-trimethylcyclohexyl)-2-buten-1-one (5) in Cold Perm Liquid and Fragrance Composition for Cold Perm using the Same Cold two-bath type perm liquids with the formulation shown in Table-2 containing thioglycolic acid as a main component were prepared using the geometrical isomer compositions of the compound (5) synthesized in Synthetic Examples.

TABLE 1

Results of scenting and stability test on geometrical isomer composition of 1-(2,2,6-trimethylcyclohexyl)-2-buten-1-one (5) in soap

| Experiment | Geometrical isomer composition of compound (5) | trans/cis | Fragrance quality A** | Fragrance quality B** | Suntan After 1 month at room temperature |
|---|---|---|---|---|---|
| 1 | Synthetic Example-7* (1R, 6S)/(1S, 6S) = | 98.7/1.3 | ⊚⊚ | ⊚○ | ⊚ |
| 2 | Synthetic Example-8* (1S, 6R)/(1R, 6S) = | 99/1 | ⊚⊚ | ⊚○ | ⊚ |
| 3 | Sythetic Example-9 Racemic modification | 99/1 | ⊚⊚ | ⊚○ | ⊚ |
| 4 | Sythetic Example-10* (1R, 6S)/(1S, 6S) = | 93/7 | ⊚⊚ | ⊚○ | ○ |
| 5 | Synthetic Example-11* (1S, 6R)/(1R, 6R) = | 93.1/6.9 | ⊚⊚ | ⊚○ | ○ |
| 6 | Sythetic Example-12 Racemic modification | 93/7 | ⊚⊚ | ⊚○ | ○ |
| 7 | Comparative Example-1* (1R, 6S)/(1S, 6S) = | 91.2/8.8 | ○○ | ○Δ | Δ |
| 8 | Comparative Example-2* (1S, 6R)/(1R, 6R) = | 91.2/8.8 | ○○ | ○Δ | Δ |
| 9 | Comparative Example-3 Racemic modification | 91.2/8.8 | ○○ | ○Δ | Δ |
| 10 | Reference Example-1 | α-Damascone | X | XX | X |
| 11 | Reference Example-2 | β-Damascone | X | XX | X |

*Optical purity: 98% e.e.
**A shows fragrance quality after 1 month at 50° C. and B shows fragrance quality after 3 months at 50° C.

As a result, damascones as Reference Example and the compositions containing 91.2% by weight of trans-isomer in Experiment Nos. 7 to 9 exhibited values which might cause some problems in fragrance stability and light stability. However, as shown in Experiment Nos. 1 to 6, 1-(2,2,6-trimethylcyclohexyl)-2-buten-1-one containing 93% by weight or more of its trans-isomer were found to be excellent in both of fragrance stability and light stability. Namely, in the case of preparing a highly tasteful fragrance composition for soap, it was revealed that a geometrical isomer compo-

TABLE 2

| Formulation of first agent of cold perm liquid | weight part |
|---|---|
| Geometrical isomer composition of compound (5) synthesized in each Synthetic Example | 0.2 |
| Ammonium thioglycolic acid | 10.0 |

TABLE 2-continued

| Formulation of first agent of cold perm liquid | weight part |
| --- | --- |
| (50% by weight aqueous solution) | |
| Aqueous ammonia | 1.5 |
| POE(20) oleyl ether (NIKKOL BO-20) | 1.0 |
| Propylene glycol | 5 |
| Sodium edetate | 0.1 |
| Purified water | 82.2 |
| Total | 100.0 |

The cold perm liquids were stored at 40° C. for 1 month or 2 months in a constant temperature chamber, and degree of masking the perm liquids and fragrance quality was investigated by three expert panelists. The results are shown in Table-3. α-Damascone and β-damascone which were tested as Reference Examples exhibited strong decomposition smell and bad masking state of ammonia at the point of time after 1 month of the test, and hence the test was discontinued at that point. With regard to the geometrical isomer compositions of 1-(2,2,6-trimethylcyclohexyl)-2-buten-1-one (5) synthesized in Synthetic Examples, it was found that those having a high trans ratio exhibit excellent stability to the base material and excellent masking ability in all the cases of racemic modification and optically active forms {(1R,6S)-isomer and/or (1S,6R)-isomer}. Namely, in the Experiments Nos. 7 to 9 using 1-(2,2,6-trimethylcyclohexyl)-2-buten-1-one (5) having a relatively low trans-isomer content of 91.2% by weight, only a slight decomposition smell was present and ammonia smell was moderately masked at the point of time after 1 month of the test. However, after 2 months, decomposition smell increased in all the cases and ammonia smell was considerably observed, and hence it was concluded that those having such a quality were impossible to use as commercial products.

On the other hand, in the test results of racemic form and optically active ones {(1R,6S)-isomer and/or (1S,6R)-isomer} having a trans-isomer content of 93% and 99% by weight, good results were obtained in all the cases (Experiments No. 1 to No. 6). As a conclusion, it was found that geometrical isomer compositions containing 93 to 99% by weight of racemic and/or optically active trans-1-(2,2,6,-trimethylcyclohexyl)-2-buten-1-one {optical isomer ratio; (1S,6R)-isomer/(1R,6S)-isomer=99/1 or 1/99} were effective for masking ammonia when a perm liquid was scented therewith. Namely, in the case of preparing a highly tasteful fragrance composition for cold perm liquids, it was revealed that a geometrical isomer composition containing 93 to 99% by weight of racemic form and/or optically active trans-1-(2,2,6-trimethylcyclohexyl)-2-buten-1-one{optical isomer ratio; (1S,6R)-isomer/(1R,6S)-isomer=99/1 or 1/99} is extremely useful as a fragrance having fruity floral fragrance.

TABLE 3

Test results of masking and stability of geometrical isomer composition of compound (5) when used in cold perm liquid
(A) Masking of ammonia smell
(B) Total evaluation

| Experiment No. | Geometrical isomer composition of compound (5) | trans/cis | Evaluation 1** (A) | (B) | Evaluation 2*** (A) | (B) |
| --- | --- | --- | --- | --- | --- | --- |
| 1 | Synthetic Example-7* (1R,6S)/(1S,6S)= | 98.7/1.3 | Good | ○ | Good | ○ |
| 2 | Synthetic Example-8* (1S,6R)/(1R,6R)= | 99/1 | Very good | ⊙ | Very good | ⊙ |
| 3 | Synthetic Example-9 Racemic modification | 99/1 | Good | ○ | Good | ○ |
| 4 | Synthetic Example-10* (1R,6S)/(1S,6S)= | 93/7 | Good | ○ | Good | ○/Δ |
| 5 | Synthetic Example-11* (1S,6R)/(1R,6R)= | 93.1/6.9 | Very good | ⊙ | Good | ○ |
| 6 | Synthetic Example-12 Racemic modification | 93/7 | Good | ○ | Good | ○ |
| 7 | Comparative Example-1* (1R,6S)/(1S,6S)= | 91.2/8.8 | Presence of slight decomp. smell | Δ | Presence of decomp. smell | X |
| 8 | Comparative Example-2* (1S,6R)/(1R,6R)= | 91.2/8.8 | Good | ○/Δ | Presence of slight decomp. smell | Δ/X |
| 9 | Comparative Example-3 Racemic modification= | 91.2/8.8 | Presence of slight decomp. smell | Δ | Presence of decomp. smell | X |
| 10 | Reference Example-1 | α-Damascone | Strong decomp. smell | X | — | |
| 11 | Reference Example-2 | β-Damascone | Strong decomp. smell | X | — | |

*Optical purity: 98% e.e.
**Results of sensory evaluation after 1 month at 40° C.
***Results of sensory evaluation after 2 months at 40° C.

TEST EXAMPLE-3

Masking and Stability Test using 1-(2,2,6-trimethylcyclohexyl)-2-buten-1-one in Hairdye Liquid and Fragrance Composition Using the Same Scented hairdye first liquids with the formulation shown in Table-4 were prepared using 1-(2,2,6-trimethylcyclohexyl)-2-buten-1-one (5) synthesized in Synthetic Examples.

TABLE 4

Formulation of hairdye first liquid

|  | weight part |
|---|---|
| p-Phenylenediamine | 2.0 |
| Aqueous ammonia | 5.0 |
| Resorcin | 1.0 |
| Polyoxyethylene cetyl ether | 3.0 |
| Cetanol | 7.0 |
| Liquid paraffin | 2.0 |
| Sodium sulfite | 0.3 |
| Sodium edetate | 0.3 |
| Geometrical isomer composition of compound (5) synthesized in each Synthetic Example | 0.2 |
| Purified water | 79.2 |
| Total | 100.0 |

The hairdye liquids were stored at 40° C. for 1 month or 2 months in a constant temperature chamber, and degree of masking ammonia smell and fragrance quality was investigated by three expert panelists. The results are shown in Table-5 and the results well resemble the results in the case of the perm liquids shown in Test Example-2. That is, α-damascone and β-damascone which were tested as Reference Examples exhibited strong decomposition smell and bad masking state of ammonia at the point of time after 1 month of the test, and thus it was reconfirmed that they are out of the question. With regard to the geometrical isomer compositions of 1-(2,2,6-trimethylcyclohexyl)-2-buten-1-one (5) synthesized in Synthetic Examples, it was reconfirmed that those having a high trans ratio exhibit good results in all the cases of racemic modification and optically active ones {(1R,6S)-isomer and/or (1S,6R)-isomer}. Namely, with regard to the trans-isomer ratio of the compound (5) and base material stability and masking ability, in the Experiments Nos. 7 to 9 using the compound (5) having a relatively low trans-isomer content of 91.2% by weight, better results were obtained at the point of time after 1 month of the test as compared with the results in the case of perm liquid and the results were judged fairly good in Experiment Nos. 7 and 9. However, after 2 months, decomposition smell was observed in all the cases and ammonia smell was not suitably masked, and hence it was concluded that those having such a quality were impossible to use as commercial products. On the other hand, in the test results of racemic form and optically active ones {(1R,6S)-isomer and/or (1S,6R)-isomer} having a trans-isomer content of 93% and 99% by weight, good results were obtained in all the cases (Experiment Nos. 1 to 6). As a conclusion, geometrical isomer compositions containing 93 to 99% by weight of racemic form and/or optically active trans-1-(2,2,6,-trimethylcyclohexyl)-2-buten-1-one {optical isomer ratio; (1S,6R)-isomer/(1R,6S)-isomer=99/1 or 1/99} were effective for masking ammonia when the hairdye liquid was scented therewith. Namely, in the case of preparing a highly tasteful fragrance composition for hairdye liquids, it was revealed that a geometrical isomer composition containing 93 to 99% by weight of racemic modification and/or optically active trans-1-(2,2,6-trimethylcyclohexyl)-2-buten-1-one {optical isomer ratio; (1S,6R)-isomer/(1R,6S)-isomer=99/1 or 1/99} is extremely useful as a fragrance having fruity floral fragrance.

TABLE 5

Test results of masking and stability of geometrical isomer composition of compound (5) when used in hairdye first liquid
(A) Masking of ammonia smell
(B) Total evaluation
(C) Test at the time when prepared
(D) Test after hairdye was used

| Experiment No. | Geometrical isomer composition of compound (5) | trans/cis | Evaluation 1** (A) | (B) | Evaluation 2*** (A) | (B) |
|---|---|---|---|---|---|---|
| 1 | Synthetic Example-7* (1R,6S)/(1S,6S)= | 98.7/1.3 | Good | ○ | Good | ○ |
| 2 | Synthetic Example-8* (1S,6R)/(1R,6R)= | 99/1 | Very good | ⊙ | Very good | ⊙ |
| 3 | Synthetic Example-9 Racemic modification | 99/1 | Good | ○ | Good | ○ |
| 4 | Synthetic Example-10* (1R,6S)/(1S,6S)= | 93/7 | Very good | ○ | Good | ○/Δ |
| 5 | Synthetic Example-11* (1S,6R)/(1R,6R)= | 93.1/6.9 | Very good | ⊙ | Very good | ⊙ |
| 6 | Synthetic Example-12 Racemic modification | 93/7 | Good | ○ | Good | ○ |
| 7 | Comparative Example-1* (1R,6S)/(1S,6S)= | 91.2/8.8 | Presence of slight decomp. smell | Δ | Presence of decomp. smell | Δ/X |
| 8 | Comparative Example-2* (1S,6R)/(1R,6R)= | 91.2/8.8 | Good | ○/Δ | Presence of slight decomp. smell | Δ |
| 9 | Comparative Example-3 Racemic modification= | 91.2/8.8 | Presence of slight decomp. smell | Δ | Presence of decomp. smell | Δ/X |

TABLE 5-continued

Test results of masking and stability of geometrical isomer composition of compound (5) when used in hairdye first liquid
(A) Masking of ammonia smell
(B) Total evaluation
(C) Test at the time when prepared
(D) Test after hairdye was used

| Experiment No. | Geometrical isomer composition of compound (5) | trans/cis | Evaluation 1** (A) | (B) | Evaluation 2*** (A) | (B) |
|---|---|---|---|---|---|---|
| 10 | Reference Example-1 | α-Damascone | Presence of decomp. smell | X | — | |
| 11 | Reference Example-2 | β-Damascone | Strong decomp. smell | X | — | |

*Optical purity: 98% e.e.
**Results of sensory evaluation after 1 month at 40° C.

TEST EXAMPLE-4

Room Air Refresher using Geometrical Isomer Composition Containing 98.7% by Weight of Optically Active trans-1-(2,2,6-trimethylcyclohexyl)-2-buten-1-one {Optical Isomer Ratio; (1R,6S)-isomer/(1S,6R)-isomer=99/1}

A highly tasteful rose fragrance with the following formulation was prepared using the geometrical isomer composition containing 98.7% by weight of optically active trans-1-(2,2,6-trimethylcyclohexyl)-2-buten-1-one (5) {optical isomer ratio; (1R,6S)-isomer/(1S,6R)-isomer=99/1} synthesized in Synthetic Example-7.

| Formulation | weight part |
|---|---|
| Geometrical isomer composition of compound (5) synthesized in Synthetic Example-7 | 15 |
| Geraniol | 110 |
| Nonylaldehyde | 2 |
| β-Ionone | 30 |
| cis-3-Hexenyl acetate | 3 |
| L-Citronellol | 80 |
| L-Citronellyl acetate | 7 |
| Phenylethylaldehyde dimethyl acetal | 50 |
| Isocyclocitral | 6 |
| L-Rose oxide | 10 |
| cis-3-Hexenol | 7 |
| Methyleugenol | 20 |
| Nerol | 20 |
| Phenylethyl acetate | 65 |
| Phenylethyl alcohol | 450 |
| Thesaron# | 100 |
| p-t-Butyldihydrocinnamaldehyde | 25 |
| Total | 1000 |

Trade name of Takasago International Corporation; ethyl 2,2,6-trimethylcyclohexylcarboxylate (the same shall apply hereinafter).

Using this fragrance composition, a room air refresher with the following formulation was prepared. The air refresher was placed in a 50-liter odorless box, which was then tightly closed. The box was allowed to stand at room temperature for 3 hours to diffuse fragrance. Thereafter, fragrance intensity of the air in the box and tastefulness were investigated by three expert panelists. Also, after used at room temperature for 1 month, quality and intensity of the fragrance were tested similarly.

| Formulation | weight part |
|---|---|
| Carrageenan | 2.0 |
| Roast bean gum | 0.2 |
| Calcium chloride | 0.2 |
| Ion-exchange water | 84.0 |
| Emulsifier | 0.3 |
| Glycol | 7.0 |
| 2,6-Di-tert-butyl-4-methylphenol (hereinafter referred to as BHT) | 0.3 |
| Fragrance composition | 6.0 |
| with the above formulation Total | 100.0 |

As a result, in the test after 1 month of use, the intensity slightly decreased, but it was revealed that the air refresher could basically overcome the problems of fragrance change and long-term persistence of fragrance (important factors for commercialization) from a sensory point of view.

TEST EXAMPLE-5

Toilet Detergent using Geometrical Isomer Composition Containing 93.1% by Weight of Optically Active trans-1-(2,2, 6-trimethylcyclohexyl)-2-buten-1-one {Optical Isomer Ratio; (1S,6R)-isomer/(1R,6S)-isomer=99/1}

For use in an acidic detergent for toilet having citrus floral fragrance tone, a citrus floral fragrance composition was prepared using the geometrical isomer composition containing 93.1% by weight of optically active trans-1-(2,2,6-trimethylcyclohexyl)-2-buten-1-one {optical isomer ratio; (1S,6R)-isomer/(1R,6S)-isomer=99/1} synthesized in Synthetic Example-11.

| Formulation | weight part |
|---|---|
| Thesaron# | 480 |
| Cinnamic alcohol | 160 |
| 2,6-Dimethylheptan-2-ol | 200 |
| 1-Methylphenchyl alcohol | 2 |
| Orange terpene | 100 |

| Formulation | weight part |
|---|---|
| Methyl salicylate | 38 |
| Geometrical isomer composition of compound | 20 |
| (5) synthesized in Synthetic Example-11 | |
| Total | 1000 |

This fragrance composition was added to a fragrance-free acidic detergent for toilet in an amount of 0.2% by weight. The mixture was placed in a plastic vessel, which was tightly closed and stored at room temperature for 90 days. Then, storage stability was investigated. As a result of judgment by three expert panelists, no change in fresh citrus floral fragrance tone was observed. Also, as a result of washing a dirty toilet, the washing effect was the same as in the case of the fragrance-free blank sample. Furthermore, in the case of the fragrance-added one, the whole toilet was filled with fresh and comfortable citrus floral fragrance after washing the toilet.

TEST EXAMPLE-6

Fragrance Composition for Mold-Removing Liquid using Geometrical Isomer Composition of Racemic 1-(2,2,6-trimethylcyclohexyl)-2-buten-1-one having a trans-isomer Content of 99% by Weight A fragrance composition for mold-removing liquid having lilac floral fragrance with the following formulation was prepared using a geometrical isomer composition of racemic 1-(2,2,6-trimethylcyclohexyl)-2-buten-1-one having a trans-isomer content of 99% by weight synthesized in Synthetic Example-9. The fragrance composition was added to a chlorate-based mold-removing liquid in an amount of 0.2% by weight. The mixture was placed in a plastic vessel, which was tightly closed and stored at 40° C. for 60 days. Then, storage stability was investigated. As a result of judgment by three expert panelists, no change in highly tasteful lilac floral fragrance tone was observed. Also, the washing effect was the same as in the case of a fragrance-free blank sample.

| Formulation | weight part |
|---|---|
| Thesaron# | 200 |
| p-Cresyl methyl ketone | 20 |
| 2,6-Dimethylheptan-2-ol | 100 |
| 1-Methylphenchyl alcohol | 20 |
| Cedryl methyl ether | 30 |
| 3,7-Dimethyloctan-3-yl ethyl ether | 600 |
| Geometrical isomer composition of compound | 30 |
| (5) synthesized in Synthetic Example-9 | |
| Total | 1000 |

While the invention has been described in detail and with reference to specific embodiments thereof, it will be apparent to one skilled in the art that various changes and modifications can be made therein without departing from the scope thereof.

This application is based on Japanese patent application No. 2002-081953 filed Mar. 22, 2002, the entire contents thereof being hereby incorporated by reference.

What is claimed is:

1. An isomer composition comprising a geometrical isomer composition containing 93 to 99% by weight of optically active trans-1-(2,2,6-trimethylcyclohexyl)-2-buten-1-one represented by Formula-1 or a mixture thereof and 7 to 1% by weight of optically active cis-1-(2,2,6-trimethylcyclohexyl)-2-buten-1-one represented by Formula-2 or a mixture thereof, respectively Formula-1

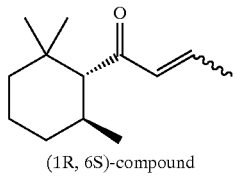 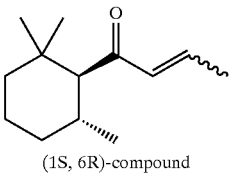

(1R, 6S)-compound     (1S, 6R)-compound

Formula-2

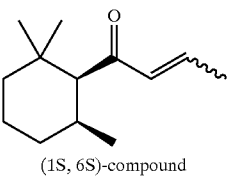 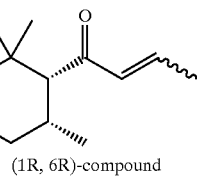

(1S, 6S)-compound     (1R, 6R)-compound

2. The isomer composition according to claim 1, wherein the mixture thereof in the optically active trans-1-(2,2,6-trimethylcyclohexyl)-2-buten-1-one or mixture thereof is racemic form of optically active trans-1-(2,2,6-trimethylcyclohexyl)-2-buten-1-one represented by Formula-1 and the mixture thereof in the optically active cis-1-(2,2,6-trimethylcyclohexyl)-2-buten-1-one or mixture thereof is racemic form of optically active cis-1-(2,2,6-trimethylcyclohexyl)-2-buten-1-one represented by Formula-2, respectively.

3. A fragrance composition comprising the isomer composition according to claim 1 or 2 and a cosmetically acceptable diluent.

4. A fragrance-scented product comprising the fragrance composition according to claim 3 as fragrance-effective component.

* * * * *